(12) United States Patent
Kinkade et al.

(10) Patent No.: US 10,617,081 B1
(45) Date of Patent: Apr. 14, 2020

(54) TETRAPLOID WATERMELON LINE 51WA009

(71) Applicant: Syngenta Crop Protection AG, Basel (CH)

(72) Inventors: Matthew Kinkade, Woodland, CA (US); James P. Brusca, Davis, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/527,276

(22) Filed: Jul. 31, 2019

(51) Int. Cl.
*A01H 5/10* (2018.01)
*A01H 6/34* (2018.01)

(52) U.S. Cl.
CPC ............... *A01H 5/10* (2013.01); *A01H 6/342* (2018.05)

(58) Field of Classification Search
CPC .................................. A01H 5/08; A01H 6/342
See application file for complete search history.

(56) References Cited

U.S. PATENT DOCUMENTS

| | | |
|---|---|---|
| 6,747,191 B2 | 6/2004 | Zhang |
| 9,066,480 B2 * | 6/2015 | Juarez ................ C12N 15/8201 |
| 9,402,357 B1 | 8/2016 | Brusca |
| 9,591,817 B1 | 3/2017 | Brusca |

OTHER PUBLICATIONS

PVP Certificate No. 200800025 issued Dec. 29, 2010.

* cited by examiner

*Primary Examiner* — Lee A Visone
(74) *Attorney, Agent, or Firm* — Karen A. Magri

(57) ABSTRACT

The present invention provides novel watermelon line 51WA009 and plant parts, seed, and tissue culture therefrom. The invention also provides methods for producing a watermelon plant by crossing the watermelon plants of the invention with themselves or another watermelon plant. The invention also provides watermelon plants produced from such a crossing as well as plant parts, seed, and tissue culture therefrom. Further provided are methods of producing triploid watermelon seed and plants and seedless watermelon fruit produced therefrom as well as the triploid watermelon seed and plants and the seedless fruits produced by such methods.

30 Claims, No Drawings

TETRAPLOID WATERMELON LINE 51WA009

FIELD OF THE INVENTION

This invention is in the field of watermelon plants, in particular, the invention relates to a novel tetraploid watermelon line, which can be used to produce triploid seeds and plants for production of seedless watermelon fruit.

BACKGROUND OF THE INVENTION

This invention relates to a new and unique inbred tetraploid watermelon line, designated 51WA009.

Watermelon is an important horticultural crop that accounts for 2% of the world area devoted to vegetable crops. There were 3,810,535 hectares (Ha) of watermelon grown in the world, and 51,110 Ha of watermelons grown in the United States in 2009. Asia is by far the most important watermelon production site with 78% of the world area and 83.4% of the world production of 100,687,056 metric tons. The estimated annual world watermelon value exceeded $7.6 billion when using the United States average price for 1995-1997. Watermelon is grown in at least forty-four states in the United States, with Florida, Georgia, California, and Texas, having long warm growing seasons, being the major producing states. In the United States, watermelon production has increased from 1.2 M tons in 1980 to 3.8 M tons in 2009, with an annual farm value of $470 million (U. S. Department of Agriculture, Agricultural Statistics, 2009).

In recent years, there has been an increase in consumer demand for seedless watermelons, and production of seedless watermelon has increased significantly. Triploid seedless watermelons have been commercially grown in the United States since the late 1980's. Currently, over 80% of the watermelons produced in the United States are triploid seedless watermelons. Seedless watermelon receives well above the average price for seeded watermelons in the market. Triploid seedless watermelon also produces higher yields than the diploid seeded watermelons.

Triploid seedless watermelon is a true F1 hybrid between a tetraploid watermelon, as the female parent, and a diploid watermelon, as the male parent (Kihara, H. 1951, *Triploid Watermelons*, Proceedings of American Society for Horticultural Science, 58:217-230). Diploid watermelons have 22 chromosomes (2N=2X=22) in their somatic cells, and tetraploid watermelons have 44 chromosomes (2N=4X=44) in their somatic cells. Cells with three sets of homologous chromosomes are said to be triploid and are designated as 3X. When female flowers of tetraploid plants are cross pollinated by the male flowers of diploid plants, the fruits produced by the tetraploid plants contain triploid seeds that produce triploid plants. The triploid seedless watermelons have 33 chromosomes (2N=3X=33) in their somatic cells. When the triploid plants are grown with diploid plants in the same field, the triploid plants produce fruits that are seedless. The seedless condition in triploid watermelon is the result of the presence of three homologous sets of chromosome per somatic cell rather than the usual two. The inability of the triploid zygote to produce normal viable gametes (pollen and egg cells) causes the absence of seeds in triploid fruits. Typically, seedless watermelons contain small edible white ovules, similar to those in immature cucumbers.

Watermelon, in general, and seedless watermelon in particular, is an important and valuable vegetable crop. Thus, there is an ongoing need for improved inbred tetraploid watermelon lines.

SUMMARY OF THE INVENTION

According to the invention, there is provided a novel inbred tetraploid watermelon line designated 51WA009, characterized by producing mature fruits having a round shape, solid light grey (Charleston Grey) skin color, intermediate rind thickness, and a dark red flesh color, and having resistance to *Fusarium* Wilt race 1. As compared with tetraploid line 4XHDML6, the mature fruits of line 51WA009 have a lower weight, are more uniform in weight and shape, and have a darker red flesh color. The invention also encompasses the seeds of watermelon line 51WA009, the plants of watermelon line 51WA009, plant parts of the watermelon line 51WA009 (including fruit, seed, gametes, scion, rootstock, shoots), methods of producing seed from watermelon line 51WA009, and methods for producing a watermelon plant by crossing the watermelon line 51WA009 with itself or another watermelon plant, methods for producing a watermelon plant containing in its genetic material one or more transgenes, and the transgenic watermelon plants produced by that method. The invention also relates to methods for producing other watermelon plants derived from watermelon line 51WA009 and to watermelon plants, parts thereof and seed produced by the use of those methods. The present invention further relates to hybrid watermelon seeds and plants (and parts thereof including fruit) produced by crossing watermelon line 51WA009 with another watermelon plant, e.g., hybrid triploid seeds and plants produced by crossing with a diploid plant.

In another aspect, the present invention provides regenerable cells for use in tissue culture of watermelon line 51WA009. In embodiments, the tissue culture is capable of regenerating plants having all or essentially all of the physiological and morphological characteristics of the foregoing watermelon plant and/or of regenerating plants having the same or substantially the same genotype as the foregoing watermelon plant. In embodiments, the regenerated plant is a tetraploid plant. In exemplary embodiments, the regenerable cells in such tissue cultures are meristematic cells, cotyledons, hypocotyl, leaves, pollen, embryos, roots, root tips, anthers, pistils, ovules, shoots, stems, petiole, pith, flowers, capsules, rootstock, scion and/or seeds as well as callus and/or protoplasts derived from any of the foregoing. Still further, the present invention provides watermelon plants regenerated from the tissue cultures of the invention.

As a further aspect, the invention provides a method of producing watermelon seed, the method comprising crossing a plant of watermelon line 51WA009 with itself or a second watermelon plant and allowing seed to form (e.g., tetraploid or triploid hybrid seed). Optionally, the method further comprises collecting the seed.

Another aspect of the invention provides methods for producing hybrids and other watermelon plants derived from watermelon line 51WA009. Watermelon plants derived by the use of these methods are also part of the invention as well as plant parts, seed, gametes and tissue culture from such hybrid or derived watermelon plants.

In representative embodiments, a watermelon plant derived from watermelon line 51WA009 comprises cells comprising at least one set of chromosomes derived from watermelon line 51WA009. In embodiments, the derived watermelon plant is a tetraploid plant. In embodiments, the derived watermelon plant is a triploid plant. In embodiments, the derived watermelon plant is a diploid plant.

In embodiments, a watermelon plant or population of watermelon plants derived from watermelon line 51WA009 comprises, on average, at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., theoretical allelic content; TAC) from watermelon line 51WA009, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of watermelon line 51WA009, and optionally may be the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and or double haploid technology. In embodiments, the derived watermelon plant is a tetraploid plant. In embodiments, the derived watermelon plant is a triploid plant. In embodiments, the derived watermelon plant is a diploid plant. In embodiments, the watermelon plant derived from watermelon line 51WA009 is one, two, three, four, five or more breeding crosses removed from watermelon line 51WA009.

In embodiments, a hybrid or derived plant from watermelon line 51WA009 comprises a desired added trait(s). In representative embodiments, a watermelon plant derived from watermelon line 51WA009 comprises all of the morphological and physiological characteristics of watermelon line 51WA009 (e.g., as described in Tables 1 to 3). In embodiments, the watermelon plant derived from watermelon line 51WA009 comprises essentially all of the morphological and physiological characteristics of watermelon line 51WA009 (e.g., as described herein), with the addition of a desired added trait(s). In embodiments, the plant derived from line 51WA009 is a tetraploid plant. In embodiments, the plant derived from line 51WA009 is a triploid plant. In embodiments, the plant derived from line 51WA009 is a diploid plant.

The invention also relates to methods for producing a watermelon plant comprising in its genetic material one or more transgenes and to the transgenic watermelon plant produced by those methods (and progeny watermelon plants comprising the transgene). Also provided are plant parts, seed and tissue culture from such transgenic watermelon plants, optionally wherein one or more cells in the plant part, seed, or tissue culture comprises the transgene. The transgene can be introduced via plant transformation and/or breeding techniques.

In another aspect, the present invention provides for single locus converted plants (e.g., diploid, triploid or tetraploid) of watermelon line 51WA009. Plant parts, seed, and tissue culture from such single locus converted plants are also contemplated by the present invention. The single locus may be a dominant or recessive allele. In representative embodiments, the single locus confers such traits as male sterility, herbicide resistance, pest resistance (e.g., insect and/or nematode resistance), modified fatty acid metabolism, modified carbohydrate metabolism, disease resistance (e.g., for bacterial, fungal and/or viral disease), male fertility, enhanced nutritional quality, improved appearance (e.g., color), improved salt tolerance, industrial usage, or any combination thereof. The single locus may be a naturally occurring watermelon locus, a genome edited locus, a mutated locus (e.g., chemically or radiation induced), or a transgene introduced into watermelon through genetic engineering techniques.

The invention further provides methods for developing watermelon plants (e.g., diploid, triploid or tetraploid) in a watermelon plant breeding program using plant breeding techniques including, for example, recurrent selection, backcrossing, pedigree breeding, double haploid techniques, restriction fragment length polymorphism enhanced selection, genetic marker enhanced selection and/or transformation. Seeds, watermelon plants, and parts thereof, produced by such breeding methods are also part of the invention.

The invention also provides methods of multiplication or propagation of watermelon plants of the invention, which can be accomplished using any method known in the art, for example, via vegetative propagation and/or seed.

Additional aspects of the invention include harvested products and processed products from the watermelon plants of the invention. A harvested product can be a whole plant or any plant part, as described herein. Thus, in some embodiments, a non-limiting example of a harvested product includes a seed, a fruit (e.g., including the flesh and/or rind), a rootstock, a scion and/or a shoot.

In representative embodiments, a processed product includes, but is not limited to: cut, sliced, ground, pureed, dried, canned, jarred, washed, packaged, frozen and/or heated fruit (including the fruit flesh and/or rind) of the watermelon plants of the invention, or any other part thereof. In embodiments, a processed product includes a sugar or other carbohydrate, fiber, protein and/or aromatic compound that is extracted, purified or isolated from a watermelon plant of the invention. In embodiments, the processed product includes washed and sliced fruit (or parts thereof, e.g., the fruit flesh with or without the rind) of the invention.

The seed of the invention can optionally be provided as an essentially homogenous population of seed of a single plant or cultivar. Essentially homogenous populations of seed are generally free from substantial numbers of other seed, e.g., at least about 90%, 95%, 96%, 97%, 98% or 99% pure.

In representative embodiments, the invention provides a seed of watermelon line 51WA009.

As a further aspect, the invention provides a plant of watermelon line 51WA009.

As an additional aspect, the invention provides a watermelon plant, or a part thereof, having all or essentially all of the physiological and morphological characteristics of a plant of watermelon line 51WA009. Optionally, the plant having all or essentially all of the physiological and morphological characteristics of a plant of watermelon line 51WA009 is a tetraploid plant.

The invention also provides plants that are diploid reversions of tetraploid watermelon line 51WA009 and parts (including seed and fruits) thereof. Also provided are methods of producing a diploid reversion derived from watermelon line 51WA009.

Also provided are methods of producing a diploid reversion of tetraploid watermelon plant of the invention. In embodiments, the method comprises crossing two plants of watermelon line 51WA009 or selfing watermelon line 51WA009, harvesting seed, and growing a diploid reversion from the harvested seed. In embodiments, the fruit and/or seed of the diploid reversion is collected. Optionally, the diploid reversion can be used in a watermelon breeding program. For example, the diploid reversion can be crossed with itself or another diploid watermelon plant to produce a further watermelon plant, fruit and seed derived from watermelon line 51WA009. In embodiments, the method further comprises doubling the chromosomes of the diploid reversion (or a diploid watermelon progeny thereof) to produce a tetraploid watermelon plant.

The invention further provides triploid watermelon seed and triploid watermelon plants (and parts thereof, such as seedless fruit) produced by crossing watermelon line 51WA009 with a diploid plant. Optionally, 51WA009 is used as the female parent.

As another aspect, the invention provides fruit and/or seed of the watermelon plants of the invention and a processed product from the fruit and/or seed of the inventive watermelon plants.

As still another aspect, the invention provides a method of producing watermelon seed, the method comprising crossing a watermelon plant of the invention with itself or a second watermelon plant. In embodiments, the method is practiced to produce seed of line 51WA009 (e.g., seed increase) by crossing the plant with itself, e.g., by open pollination of the variety. The invention also provides seed produced by this method and plants, and parts thereof including fruit, produced by growing the seed.

As yet a further aspect, the invention provides a method for producing a seed of a watermelon plant derived from watermelon line 51WA009, the method comprising: (a) crossing a watermelon plant of watermelon line 51WA009 with a second watermelon plant; and (b) allowing seed of a watermelon plant derived from watermelon line 51WA009 to form. In embodiments, the method further comprises: (c) growing a plant from the seed derived from watermelon line 51WA009 of step (b); (d) selfing the plant of step (c) or crossing it to a second watermelon plant to form additional watermelon seed derived from watermelon line 51WA009, and (e) optionally repeating steps (c) and (d) one or more times to generate further derived watermelon seed from watermelon line 51WA009, wherein in step (c) a plant is grown from the additional watermelon seed of step (d) in place of growing a plant from the seed of step (b). In embodiments, the method comprises: (e) repeating steps (c) and (d) one or more times (e.g., one to three, one to five, one to six, one to seven, one to ten, three to five, three to six, three to seven, three to eight or three to ten times) to generate further derived watermelon seed. As another option, the method can comprise collecting the seed. The invention also provides seed produced by these methods and watermelon plants (e.g., tetraploid watermelon plants) produced by growing the seed.

Still further, as another aspect, the invention provides a method of vegetatively propagating a plant of watermelon line 51WA009, e.g., via shoot proliferation and then rooting in tissue culture. Detailed methods were described by Zhang et al. (Zhang, X. P., B. B. Rhodes, H. T. Skorupska, W. C. Bridges. 1995. Generating Tetraploid Watermelon Using Colchicine in Vitro. G. Lester & J. Dunlap et al. (eds.), Cucurbitaceae' 94: 134-139). In a non-limiting example, the method comprises: (a) collecting tissue capable of being propagated from a plant of watermelon line 51WA009; (b) cultivating the tissue to obtain proliferated shoots; and (c) rooting the proliferated shoots to obtain rooted plantlets. Optionally, the invention further comprises growing plants from the rooted plantlets. The invention also encompasses the plantlets and plants produced by these methods.

As an additional aspect, the invention provides a method of introducing a desired added trait into watermelon line 51WA009, the method comprising: (a) crossing a first plant of watermelon line 51WA009 with a second watermelon plant that comprises a desired trait to produce $F_1$ progeny; (b) selecting an $F_1$ progeny that comprises the desired trait; (c) crossing the selected $F_1$ progeny with watermelon line 51WA009 to produce backcross progeny; and (d) selecting backcross progeny comprising the desired trait to produce a plant derived from watermelon line 51WA009 comprising a desired trait.

In embodiments, the selected progeny produces a round fruit. In embodiments, the selected progeny produces a mature fruit having an intermediate rind thickness. In embodiments, the selected progeny produces a mature fruit having a solid light grey (e.g., Charleston Grey) skin. In embodiments, the selected progeny produces a mature fruit with a dark red flesh (e.g., darker red as compared with line 4XHDML6). In embodiments, the selected progeny produces a mature fruit with a lower weight as compared with comparison variety 4XHDML6. In embodiments, the selected progeny produces a mature fruit with a more uniform weight and/or shape as compared with comparison variety 4XHDML6. In embodiments, the selected progeny has resistance to *Fusarium* wilt race 1. In embodiments, the selected progeny comprises all or essentially all the morphological and physiological characteristics of watermelon line 51WA009 (e.g., a described in Tables 1 to 3). Optionally, the method further comprises: (e) repeating steps (c) and (d) one or more times (e.g., one to three, one to five, one to six, one to seven, one to ten, three to five, three to six, three to seven, three to eight or three to ten times) to produce a plant derived from watermelon line 51WA009 comprising the desired trait, wherein in step (c) the selected backcross progeny produced in step (d) is used in place of the selected F1 progeny of step (b). In embodiments, the plant derived from line 51WA009 and comprising the desired added trait is a tetraploid plant. In embodiments, the plant derived from line 51WA009 and comprising the desired added trait is a triploid plant. In embodiments, the plant derived from line 51WA009 and comprising the desired added trait is a diploid plant.

In representative embodiments, the invention also provides a method of producing a plant of watermelon line 51WA009 comprising a desired added trait, the method comprising introducing a transgene conferring the desired trait into a plant of watermelon line 51WA009. The transgene can be introduced by transformation methods (e.g., genetic engineering) or breeding techniques. In embodiments, the plant comprising the transgene produces a round fruit. In embodiments, the plant comprising the transgene produces a mature fruit having an intermediate rind thickness. In embodiments, the plant comprising the transgene produces a mature fruit having a solid light grey (e.g., Charleston Grey) skin. In embodiments, the plant comprising the transgene produces a mature fruit with a dark red flesh (e.g., darker red as compared with line 4XHDML6). In embodiments, the plant comprising the transgene produces a mature fruit with a lower weight as compared with comparison variety 4XHDML6. In embodiments, the plant comprising the transgene produces a mature fruit with a more uniform weight and/or shape as compared with comparison variety 4XHDML6. In embodiments, the plant comprising the transgene has *Fusarium* wilt race 1 resistance, and optionally is a tetraploid plant. In embodiments, the plant comprising the transgene comprises all or essentially all of the morphological and physiological characteristics of watermelon line 51WA009 (e.g., as described in Tables 1 to 3).

The invention also provides watermelon plants (e.g., a diploid, triploid or tetraploid watermelon plant) produced by the methods of the invention, wherein the watermelon plant has the desired added trait as well as seed and fruits from such watermelon plants. The invention also provides seed that produces the plants derived from line 51WA009 and comprising a desired added trait.

According to the foregoing methods, the desired added trait can be any suitable trait known in the art including, for example, male sterility, male fertility, herbicide resistance, insect or pest (e.g., insect and/or nematode) resistance, modified fatty acid metabolism, modified carbohydrate metabolism, disease resistance (e.g., for bacterial, fungal and/or viral disease), enhanced nutritional quality, increased sweetness, increased flavor, improved ripening control, improved salt tolerance, industrial usage, or any combination thereof.

In representative embodiments, a transgene conferring herbicide resistance confers resistance to glyphosate, sulfonylurea, imidazolinone, dicamba, glufosinate, phenoxy proprionic acid, L-phosphinothricin, cyclohexone, cyclohexanedione, triazine, benzonitrile, or any combination thereof.

In representative embodiments, a transgene conferring pest resistance (e.g., insect and/or nematode resistance) encodes a *Bacillus thuringiensis* endotoxin.

In representative embodiments, transgenic plants, single locus converted plants, hybrid plants and watermelon plants derived from watermelon line 51WA009 are characterized by, e.g., one or more of tetraploidy, round fruits, mature fruits having a solid light grey (e.g., Charleston grey) skin color, mature fruits having an intermediate rind thickness, mature fruits having dark red flesh (e.g., darker red as compared with line 4XHDML6), mature fruits with a lower weight than the mature fruits of line 4XHDML6, mature fruits that are more uniform in weight and/or shape than the mature fruits of line 4XHDML6, and/or resistance to *Fusarium* wilt race 1. In representative embodiments, transgenic plants, single locus converted plants, hybrid plants and watermelon plants derived from watermelon line 51WA009 have at least 3, 4, 5, 6, 7, 8, 9, 10 or more of the morphological and physiological characteristics of watermelon line 51WA009 (for example, one or more of tetraploidy, round fruits, mature fruits having a solid light grey (e.g., Charleston grey) skin color, mature fruits having an intermediate rind thickness, mature fruits having dark red flesh (e.g., darker red as compared with line 4XHDML6), mature fruits with a lower weight than the mature fruits of line 4XHDML6, mature fruits that are more uniform in weight and/or shape than the mature fruits of line 4XHDML6, and/or resistance to *Fusarium* wilt race 1, e.g., as described in Tables 1 to 3), or even all of the morphological and physiological characteristics of watermelon line 51WA009, so that said plants are not significantly different for said traits than watermelon line 51WA009, as determined at the 5% significance level when grown in the same environmental conditions; optionally, with the presence of one or more desired additional traits (e.g., male sterility, disease resistance, pest or insect resistance, herbicide resistance, and the like).

As a further aspect, the invention provides a method of producing triploid watermelon seed, the method comprising: (a) crossing a watermelon plant of line 51WA009 with a diploid watermelon plant; and (b) optionally, harvesting the resultant triploid watermelon seed. In embodiments, the plant of line 51WA009 is the female parent and the diploid parent is the male plant (i.e., pollenator). Also provided is a hybrid triploid watermelon seed produced by the foregoing method, and a triploid watermelon plant (and parts thereof, including seedless fruit) grown from the triploid seed.

The invention also provides as another aspect, a method of producing seedless watermelon fruit, the method comprising: (a) crossing the triploid watermelon plant produced by the method of the preceding paragraph and a diploid watermelon plant; (b) allowing a seedless fruit to form; and (c) optionally, harvesting the seedless fruit. In embodiments, the plant of line 51WA009 is the female parent and the diploid parent is the male plant (i.e., pollenator). Also provided is a seedless watermelon fruit produced by the foregoing method.

As still a further aspect, the invention provides a tetraploid watermelon plant, or a part thereof, produced by crossing a 51WA009 plant with a different tetraploid watermelon plant (e.g., a tetraploid inbred or hybrid plant).

The invention further provides a method of developing a tetraploid watermelon line in a watermelon plant breeding program using plant breeding techniques, which include employing a watermelon plant, or a part thereof, as a source of plant breeding material, the method comprising: (a) obtaining the watermelon plant, or a part thereof, of line 51WA009 as a source of breeding material; and (b) applying plant breeding techniques.

The invention also encompasses plant parts, plant material, pollen, ovules, leaves, fruit and seed from the watermelon plants of the invention. The invention also provides seed that produces the watermelon plants of the invention. Also provided is a tissue culture of regenerable cells from the watermelon plants of the invention, where optionally, the regenerable cells are: (a) embryos, meristem, leaves, pollen, cotyledons, hypocotyls, roots, root tips, anthers, flowers, pistils, ovules, seed, shoots, stems, stalks, petioles, pith and/or capsules; or (b) callus or protoplasts derived from the cells of (a). Further provided are watermelon plants regenerated from a tissue culture of the invention.

In still yet another aspect, the invention provides a method of determining a genetic characteristic of watermelon line 51WA009 or a progeny thereof, e.g., a method of determining a genotype of watermelon line 51WA009 or a progeny thereof using molecular genetic techniques. In embodiments, the method comprises detecting in the genome of a 51WA009 plant, or a progeny plant thereof, at least a first polymorphism, e.g., comprises nucleic acid amplification and/or nucleic acid sequencing. To illustrate, in embodiments, the method comprises obtaining a sample of nucleic acids from the plant and detecting at least a first polymorphism in the nucleic acid sample (e.g., using one or more molecular markers). Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

In addition to the exemplary aspects and embodiments described above, the invention is described in more detail in the description of the invention set forth below.

DETAILED DESCRIPTION OF THE INVENTION

The present invention is based, in part, on the development of a novel watermelon characterized by producing mature fruits having a round shape, solid light grey (Charleston Grey) skin color, intermediate rind thickness, and a dark red flesh color, having resistance to *Fusarium* Wilt race 1. As compared with tetraploid line 4XHDML6, the mature fruits of line 51WA009 have a lower weight, are more uniform in weight and shape, and have a darker red flesh color.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless the context indicates otherwise, it is specifically intended that the various features and embodiments of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

Definitions

In the description and tables that follow, a number of terms are used. In order to provide a clear and consistent understanding of the specification and claims, including the scope to be given such terms, the following definitions are provided:

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP § 2111.03. Thus, the term "consisting essentially of" when used in a claim or the description of this invention is not intended to be interpreted to be equivalent to "comprising."

Those skilled in the art will appreciate that when a comparison of physiological and morphological characteristics between two or more varieties is made, it is assumed that the varieties are grown under the same environmental conditions, whether in the field or green house. In addition, such comparisons are generally made on the basis of observations taken on a population of plants, which define the characteristics of the variety.

"Allele". An allele is any of one or more alternative forms of a gene, all of which relate to a trait or characteristic. In a diploid cell or organism, the two alleles of a given gene occupy corresponding loci on a pair of homologous chromosomes.

"Backcrossing". Backcrossing is a process in which a breeder repeatedly crosses hybrid progeny back to one of the parents, for example, a first generation hybrid $F_1$ with one of the parental genotype of the $F_1$ hybrid.

"Cotyledon". One of the first leaves of the embryo of a seed plant; typically one or more in monocotyledons, two in dicotyledons, and two or more in gymnosperms.

"Double haploid line". A stable inbred line achieved by doubling the chromosomes of a haploid line, e.g., from anther culture. For example, some pollen grains (haploid) cultivated under specific conditions develop plantlets containing 1 n chromosomes. The chromosomes in these plantlets are then induced to "double" (e.g., using chemical means) resulting in cells containing 2n chromosomes. The progeny of these plantlets are termed "double haploid" and are essentially not segregating any more (e.g., are stable). The term "double haploid" is used interchangeably herein with "dihaploid."

"Essentially all the physiological and morphological characteristics". A plant having "essentially all the physiological and morphological characteristics" (and similar phrases) means a plant having all of the desired physiological and morphological characteristics of variety 51WA009, except for the characteristic(s) derived from a converted locus/loci (e.g., a single converted locus), for example, introduced via backcrossing to variety 51WA009, a modified gene(s) resulting from genome editing techniques, an introduced transgene (i.e., introduced via genetic transformation techniques) or mutation, when both plants are grown under the same environmental conditions. In embodiments, a plant having "essentially all of the physiological and morphological characteristics" means a plant having all of the characteristics of the reference plant with the exception of five or fewer traits, 4 or fewer traits, 3 or fewer traits, 2 or fewer traits, or one trait. In embodiments, the plant comprising "essentially all of the physiological and morphological characteristics" of variety 51WA009 produces a mature fruit with a round shape, solid light grey (Charleston Grey) skin color, intermediate rind thickness, and a dark red flesh color (e.g., darker red as compared with tetraploid line 4XHDML6, when both plants are grown under the same environmental conditions) and has resistance to *Fusarium* Wilt race 1, and is optionally diploid or tetraploid. In embodiments, a plant comprising "essentially all of the physiological and morphological characteristics" of variety 51WA009 comprises the traits of Tables 1 to 3.

"First water date". The date the seed first receives adequate moisture to germinate. This can and often does equal the planting date.

"Gene". As used herein, "gene" refers to a segment of nucleic acid comprising an open reading frame. A gene can be introduced into a genome of a species, whether from a different species or from the same species, using transformation or various breeding methods.

"Inbred line": As used herein, the phrase "inbred line" refers to a genetically homozygous or nearly homozygous population. An inbred line, for example, can be derived through several cycles of sib crossing and/or selfing and/or via double haploid production. In some embodiments, inbred lines breed true for one or more traits of interest. An "inbred plant" or "inbred progeny" is an individual sampled from an inbred line.

"Plant." As used herein, the term "plant" includes plant cells, plant protoplasts, plant cell tissue cultures from which plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, fruit, stems, rootstock, scion, and the like.

"Plant material". The terms "plant material" and "material obtainable from a plant" are used interchangeably herein and refer to any plant material obtainable from a plant including without limitation, leaves, stems, roots, flowers or flower parts, fruits, pollen, ovules, zygotes, seeds, cuttings, cell or tissue cultures, rootstocks, scions, or any other part or product of the plant.

"Plant part". As used herein, a "plant part" includes any part, organ, tissue or cell of a plant including without limitation an embryo, meristem, leaf, pollen, cotyledon, hypocotyl, root, root tip, anther, flower, flower bud, pistil, ovule, seed, shoot, stem, stalk, petiole, pith, capsule, a scion, a rootstock and/or a fruit including callus and protoplasts derived from any of the foregoing. In representative embodiments, the plant part is a non-propagating plant part, for example, is not a seed.

"Quantitative Trait Loci". Quantitative Trait Loci (QTL) refers to genetic loci that control to some degree, numerically representable traits that are usually continuously distributed.

"Regeneration". Regeneration refers to the development of a plant from tissue culture.

"Resistance". As used herein the terms "resistance" and "tolerance" (and grammatical variations thereof) are used interchangeably to describe plants that show reduced or essentially no symptoms to a specific biotic (e.g., a pest, pathogen or disease) or abiotic (e.g., exogenous or environmental, including herbicides) factor or stressor. In some embodiments, "resistant" or "tolerant" plants show some symptoms but are still able to produce marketable product with an acceptable yield, e.g., the yield may still be reduced and/or the plants may be stunted as compared with the yield or growth in the absence of the biotic and/or abiotic factor or stressor. Those skilled in the art will appreciate that the degree of resistance or tolerance may be assessed with respect to a plurality or even an entire field of plants. A watermelon plant may be considered "resistant" or "tolerant" if resistance/tolerance is observed over a plurality of plants (e.g., an average), even if particular individual plants may be susceptible to the biotic or abiotic factor or stressor.

"RHS". RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

"Single locus converted". A single locus converted or conversion plant refers to a plant that is developed by plant breeding techniques (e.g., backcrossing), genome editing techniques, genetic transformation techniques and/or mutation techniques wherein essentially all of the desired morphological and physiological characteristics of a line are recovered in addition to the single locus introduced into the line via the plant breeding, genome editing, genetic transformation, or mutation techniques.

As used herein, a "small" watermelon fruit refers to a mean fruit weight that is less than about 8 kg, 7 kg, 6 kg, 5 kg, 4.5 kg or even 4 kg.

"Substantially equivalent characteristic". A characteristic that, when compared, does not show a statistically significant difference (e.g., $p=0.05$) from the mean.

"Thousand seed weight" as used herein refers to the average weight of 1000 seeds of the variety. In embodiments, the plant or variety has a "low" or "relatively low" thousand seed weight, e.g., less than about 55, 50, 45, 44, 43, 42, 41 or 40 grams per thousand seeds (e.g., untreated seeds).

"Transgene". A nucleic acid of interest that can be introduced into the genome of a plant by genetic engineering techniques (e.g., transformation) or breeding. The transgene can be from the same or a different species. If from the same species, the transgene can be an additional copy of a native coding sequence or can present the native sequence in a form or context (e.g., different genomic location and/or in operable association with exogenous regulatory elements such as a promoter) than is found in the native state. The transgene can comprise an open reading frame encoding a polypeptide or can encode a functional non-translated RNA (e.g., RNAi).

Botanical Description of the Watermelon Line 51WA009.

Characteristics. New watermelon inbred tetraploid line 51WA009 is characterized by producing mature fruits having a round shape, solid light grey (Charleston Grey) skin color, intermediate rind thickness, and a dark red flesh color, and is resistant to *Fusarium* Wilt race 1. As compared with tetraploid line 4XHDML6 (United States PVP Certificate No. 200800025), the mature fruits of line 51WA009 have a lower weight, are more uniform in weight and shape, and have a more intense and darker red flesh color. This combination of traits is unique to 51WA009. Line 4XHDML6 was selected as the most similar variety for comparison because it is a tetraploid line with intermediate resistance to *Fusarium* wilt race 1 and has a similar fruit shape, size and rind color as compared with line 51WA009.

Test crosses of triploid hybrids produced using 51WA009 as female parent have been evaluated. Promising triploid hybrids have been selected for multiple location trials. 51WA009 is a new, unique and useful elite inbred tetraploid line for producing triploid seedless hybrids.

Watermelon line 51WA009 has shown uniformity and stability within the limits of environmental influence. It has been self-pollinated for numerous generations with careful attention to uniformity of plant type. The variety has been increased with continued observation for uniformity. No variant traits have been observed or are expected in watermelon line 51WA009.

A more detailed botanical description of 51WA009 and comparison with 4XHDML6 is shown in Table 1 below.

TABLE 1

Description of 51WA009 and comparison with 4XHDML6 based on openfield trials in Naples, Florida.

| Characteristic: | 51WA009 | 4XHDML6 |
| --- | --- | --- |
| General fruit type: | round small | round small |
| Area of best adaptation: | most areas | most areas |
| Maturity-No. of days from pollination to maturity: | 42.2 days | 40.9 days |
| Maturity category: | medium | medium |
| Ploidy: | tetraploid | tetraploid |
| Cotyledon shape: | flat | flat |
| Plant sex form: | monoecious | monoecious |
| Number of flowers per plant at first fruit set: | 2.2 staminate, 0.2 pistillate, 0 perfect | 2.9 staminate, 0.89 pistillate, 0 perfect |
| Stem: | round (cross-section), pubescent | round (cross-section), pubescent |
| Vine length at last harvest: | 260 cm | 294 cm |

TABLE 1-continued

Description of 51WA009 and comparison with 4XHDML6 based on openfield trials in Naples, Florida.

| Characteristic: | 51WA009 | 4XHDML6 |
|---|---|---|
| No. internodes at last harvest: | 35.1 | 38.3 |
| Ratio: cm vine length/internodes at last harvest: | 3.29 | 3.21 |
| Leaf shape: | ovate | ovate |
| Leaf lobes: | lobed | lobed |
| Leaf length: | 18.4 cm | 17.6 cm |
| Leaf width: | 19.5 cm | 18 cm |
| Leaf dorsal surface pubescence: | pubescent | pubescent |
| Leaf ventral surface pubescence: | pubescent | pubescent |
| Leaf color: | medium green | medium green |
| Flower: | staminate, 3.2 cm across; pistillate, 2.6 cm across; yellow (RHS 7D) | Staminate, 3.4 cm across; pistillate, 1.9 cm across; yellow (RHS 7D) |
| Mature fruit: | round, 21.5 cm long, 21.3 cm diameter at midsection, 1.68 kg average weight, 2.4 kg maximum weight, smooth surface, solid light green (Charleston Grey) skin color | round, 22.4 cm long, 23 cm diameter at midsection, 2.14 kg average weight, 2.9 kg maximum weight, smooth surface, solid light green (Charleston Grey) skin color |
| Rind: | tough, 16 mm thick at sides | tough, 15 mm thick at sides |
| Flesh: | crisp flesh texture, fine with little fiber, dark red (RHS 47D), 12.8% soluble solids of juice at center of fruit (refractometer), 30% hollow heart, 100% placental separation, no transverse cracking observed | crisp flesh texture, fine with little fiber, red (RHS 48C), 10.8% soluble solids of juice at center of fruit (refractometer), 20% hollow heart, 100% placental separation, no transverse cracking observed |
| Seed (F1 seed; no seed in F1 fruit): | medium, 9.2 mm long, 6.5 mm wide, 2.1 mm thick, index is 14.3 (length ÷ width × 10), 40.8 gm per 1000 seeds, 37 seeds per fruit, tan color | medium, 9.3 mm long, 6.4 mm wide, 1.7 mm thick, index is 14.6 (length ÷ width × 10), 39.3 gm per 1000 seeds, 42 seeds per fruit, tan color |
| Anthracnose, Race 1: | susceptible | susceptible |
| Fusarium Wilt, Race 1: | resistant | resistant |

51WA009 has resistance to *Fusarium* wilt race 1, conferred by the gene Fo-1 (Henderson, W. R., S. F. Jenkins, Jr., and J. O. Rawlings. 1970. The inheritance of *Fusarium* wilt resistance in watermelon, *Citrullus lanatus* (Thunb.) Mansf. J. Amer. Soc. Hort. Sci. 95: 276-282). As demonstrated in the standard pathology test results shown in Table 2 below, Black Diamond does not carry the resistance allele at the Fo-1 locus and is susceptible to *Fusarium* wilt race 1, whereas 51WA009 carries the resistance allele at the Fo-1 locus and is resistant to *Fusarium* wilt race 1.

TABLE 2

Aggregate results of resistance to *Fusarium oxysporum* sp. *niveum* (FON) race 1[1] in 51WA009 and controls in seedling assays carried out across 2 years.

| Variety | Resistant | Susceptible | Resistant | Results |
|---|---|---|---|---|
| 51WA009 | 182 | 8 | 95.8 | Resistant |
| SP-6 | 59 | 0 | 100 | Resistant |
| Calhoun Grey | 196 | 1 | 99.5 | Resistant |

TABLE 2-continued

Aggregate results of resistance to *Fusarium oxysporum* sp. *niveum* (FON) race 1[1] in 51WA009 and controls in seedling assays carried out across 2 years.

| Variety | Resistant | Susceptible | Resistant | Results |
|---|---|---|---|---|
| Black Diamond | 7 | 48 | 12.7 | Susceptible |

[1]Race 1 isolate 811B was used for this assay.

Variety 51WA009 possesses unique aspects of fruit quality when compared with line 4XHDML6, as shown in Table 3. 51WA009 has lower fruit weight and less variability in fruit weight as compared with 4XHDML6. Line 51WA009 also has lower plant vigor, intermediate rind thickness, and a darker red flesh as compared with 4XHDML6. This combination of traits is unique in 51WA009.

TABLE 3

Comparison of fruit weight and internal quality characteristics of lines 51WA009 and 4XHDML6 across 3 years in Naples, FL and Woodland, CA.

| | Mean Fruit Weight (kg)[1] | Median Fruit Weight (kg) | Standard Deviation of Mean Fruit Weight (kg) | Plant Vigor at Harvest (1-9 scale)[2] | Rind Thickness at Maturity (cm)[3] | Flesh Color Intensity at Maturity (1-9 scale)[4] |
|---|---|---|---|---|---|---|
| 4XHDML6 | 2.14 | 2.24 | 0.38 | 5.67 | 1.36 | 5.38 |
| 51WA009 | 1.68 | 2.13 | 0.36 | 5.00 | 1.11 | 6.40 |

[1]Mean fruit weight was calculated from a population of fruits harvested.
[2]Plant vigor is rated on a scale of 1 to 9, with 9 being highly vigorous.
[3]Rind thickness at maturity is measured on a population of harvested fruits.
[4]Flesh color intensity is rated on a scale of 1 to 9, with 9 being very dark red.

Tissue Culture.

In embodiments, watermelon plants can be propagated by tissue culture and regeneration. Tissue culture of various plant tissues and regeneration of plants therefrom is well known. For example, reference may be had to Teng, et al., HortScience, 27:9, 1030-1032 (1992); Teng, et al., HortScience, 28:6, 669-1671 (1993); Zhang, et al., Journal of Genetics and Breeding, 46:3, 287-290 (1992); Webb, et al., Plant Cell Tissue and Organ Culture, 38:1, 77-79 (1994); Curtis, et al., Journal of Experimental Botany, 45:279, 1441-1449 (1994); Nagata, et al., Journal for the American Society for Horticultural Science, 125:6, 669-672 (2000); and Ibrahim, et al., Plant Cell Tissue and Organ Culture, 28(2), 139-145 (1992). It is clear from the literature that the state of the art is such that these methods of obtaining plants are routinely used and have a high rate of success. Thus, another aspect of this invention is to provide cells which upon growth and differentiation produce watermelon plants having desired characteristics of watermelon line 51WA009 (e.g., one or more of one or more of tetraploidy, round fruits, mature fruits having a solid light grey (e.g., Charleston grey) skin color, mature fruits having an intermediate rind thickness, mature fruits having dark red flesh (e.g., darker red as compared with line 4XHDML6), mature fruits with a lower weight than the mature fruits of line 4XHDML6, mature fruits that are more uniform in weight and/or shape than the mature fruits of line 4XHDML6, and/or resistance to *Fusarium* wilt race 1). Optionally, watermelon plants can be regenerated from the tissue culture of the invention comprising all or essentially all of the physiological and morphological characteristics of watermelon line 51WA009.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques.

Tetraploid Watermelon Lines and Triploid Seed Production

The primary use of tetraploid watermelons is to make triploid hybrid watermelon seeds and plants that produce seedless fruit. In commercial production of triploid watermelon seed, tetraploid and diploid parental lines are typically planted in the same field. Cross-pollination between the tetraploid line, generally used as the female parental line, and the diploid line, the male parental line, are accomplished by either hand or bee pollination. Triploid watermelon seeds are produced only in fruits of tetraploid plants that are fertilized with pollen of diploid plants. All commercially grown seeded watermelons are diploid; therefore, there are many diploid lines for use as diploid parents. The major limitation to development of seedless watermelon varieties lies in the availability of useful elite tetraploid parental lines.

Tetraploid watermelon lines can be developed from diploid lines by doubling the chromosomes of diploid watermelon lines using methods routine in the art. Chromosome doubling was first accomplished with the alkaloid colchicine by applying colchicine to the growing point of newly emerged watermelon seedlings. Tissue culture methods have also been developed (Zhang, X. P., B. B. Rhodes, H. T. Skorupska, W. C. Bridges, 1995, *Generating Tetraploid Watermelon Using Colchicine in Vitro*, G. Lester & J. Dunlap et al. (eds.), Cucurbitaceae' 94: 134-139). Dinitroanilines have been used to double chromosome numbers, and their effectiveness has previously been compared with crops other than watermelon. Li et al. compared in vitro chromosome doubling effectiveness using colchicine and the dinitroanilines, ethalfluralin (N-ethyl-N-2-methyl-2-propenyl)-2,6-dinitro-4-(trifluoromethyl) benzanine), and oryzalin (3,5-dinitro-N4, N4-dipropylsulfanilamide) and concluded that either ethalfluralin or oryzalin was preferable to colchicine (Li, Ying, J. F. Whitesides, B. Rhodes, 1999, *In vitro generation of tetraploid watermelon with two different dinitroanilines and colchicines*, Cucurbit Genetics Cooperative Rpt 22:38-40).

Several treatment methods can be used to induce tetraploids from diploids using the chemicals mentioned above. One exemplary method is to treat the seed before sowing. The seed are soaked in clean water for 5-6 hrs and then the seed are soaked in either colchicine solution (0.2%) or dinitroanilines (e.g. 35 µM oryzalin) for 24 hrs. The seed are briefly rinsed before sowing. Dry seed can also be directly soaked in the chemical solution without pre-soaking in the water. The treatment usually reduces the germination and emergence. A second method is to treat the newly emerged seedling. To illustrate, the diploid inbreds can be sown in the greenhouse in seedling flats. The soil temperature is kept at 29-31° C. for rapid and uniform germination. One drop of colchicine (0.1%) or dinitroanilines (e.g. 35 µM oryzalin) solution is added to the shoot apex between the cotyledons as soon as the seedling has emerged from soil. The colchicine solution is applied to the growing point in the morning or evening for three consecutive days. Good chromosome doubling is achieved from application of oryzalin. Another illustrative method is to treat the shoot apex of germinated seed after which the germinated seed is planted into soil. The seeds are germinated in an incubator at 30° C. When the radicals are about 2 cm long, the portion above the hypocotyls of germinated seeds is immersed upside down into colchicine (0.1%) or dinitroaniline solution (35 µM oryzalin) for 10-15 hrs at 30° C. in an incubator. The treatment is typically conducted in a high humidity chamber or box to assure that the radicals/roots are not desiccated. The seeds are then washed and planted in the soil. The last two methods, although more tedious to use, usually give better recovery of tetraploid events as the root system is not affected by the treatment.

The next step is to develop tetraploid lines from individual converting events. For example, the selected tetraploid individuals based on morphological expression can be self-pollinated and the resulting seeds planted in the next generation as lines. These lines can again be self-pollinated and compared for fertility and horticultural traits. Only the desirable lines are selected if there is difference among these lines. Desirable lines may be bulk harvested if there is no variation within the line and among selected lines. Further seed increases may be conducted in an isolation block. Mass selection may be conducted for this increase in the isolation plot and thereafter. Fertility of the tetraploid may be improved in subsequent generations.

The use of tissue culture to propagate tetraploid watermelon plants is exemplified in Adelberg, J. W., B. B. Rhodes, *Micropropagation from zygotic tissue of watermelon*, C. E. Thomas (ed.) Proc. of the Cucurbitaceae 89: *Evaluation and enhancement of cucurbit germplasm*, Charleston S.C., USA; and Zhang et al., *Shoot regeneration from immature cotyledon of watermelon*, Cucurbit Genetics Coop. 17:111-115 (1994).

Crossing two different tetraploids and then going through recombination breeding can also result in new tetraploid lines. A longer breeding period is typically employed to develop a stable tetraploid line using this approach because of the larger number of combinations and the fewer seed that tetraploids produce. However, some breeders have made good progress by taking this approach.

Because meiosis is sometimes irregular in autotetraploids, there can be diploids and aneuploids among the offspring. The leaves, flowers and pollen grains of tetraploids are morphologically distinct from diploids (Zhang, X. P., B. B. Rhodes, H. T. Skorupska, W. C. Bridges, 1995, *Generating Tetraploid Watermelon Using Colchicine in Vitro*, G. Lester & J. Dunlap et al. (eds.), Cucurbitaceae' 94: 134-139). Tetraploids also have a different number of chloroplasts in the guard cells (Compton, M. E., D. J. Gray and G. W. Elmstrom. 1996, *Identification of tetraploid regenerants from cotyledons of diploid watermelon cultures in vitro*, Euphytica 87:165-172). These morphological traits can help the breeder eliminate the diploids and aneuploids occurring in the tetraploid population during sexual propagation. Diploid reversions can also be identified in situations in which a diploid derived from line 51WA009 is desired, and such diploid reversions are also encompassed by the present invention.

Accordingly, the invention contemplates as one aspect a method of producing triploid watermelon seed, the method comprising: (a) crossing the watermelon plant of line 51WA009 with a diploid watermelon plant; and (b) harvesting the resultant triploid watermelon seed. In embodiments the plant of line 51WA009 is the female parent and the diploid plant is the male parent. In embodiments, the plant of line 51WA009 is the male parent and the diploid plant is the female parent. The triploid watermelon seed produces a triploid plant, which when grown into a plant produces a seedless watermelon fruit (i.e., when crossed with a diploid plant).

The invention further provides a method of producing seedless watermelon fruit, the method comprising: (a) crossing a triploid plant produced from line 51WA009 (e.g., an F1 hybrid of 51WA009 produced as described in the preceding paragraph) and a diploid watermelon plant; (b) allowing seedless fruit to form; and (c) optionally, harvesting the seedless fruit. In embodiments, the triploid watermelon seed and seed from a diploid plant are planted in one or more rows, and the plants are allowed to mature and develop seedless fruit. In embodiments, diploid and triploid seed are planted in the same row. In embodiments the triploid plant is the female parent and the diploid plant is the male parent. In embodiments, the triploid plant is the male parent and the diploid plant is the female parent.

Several methods can be used to produce triploid seeds from inbred 51WA009. Two commonly used methods are described below. Variations to these methods can be made according to the actual production situation.

Hand-Pollination Method

Hand pollination can be used for producing triploid seed from 51WA009. For example, in embodiments, the inbred tetraploid female parent 51WA009 and the inbred diploid male parent line are planted in the same field. To illustrate, in an exemplary method, the inbred male parent is planted 7-10 days earlier than the female parent 51WA009 to insure adequate pollen supply at the pollination time. The male parent and female parent 51WA009 can be planted, for example, in the ratio of 1 male parent to 4-10 female parents. Optionally, the diploid male parent is planted at the top of the field for efficient male flower collection during pollination. Pollination is generally started when the second female flower on the tetraploid female parent 51WA009 is ready to flower. Female flower buds that are ready to open the next day are identified, covered with paper cups or small paper bags that prevent bee or any other insect visit of the female flowers, and marked with any kind of material that can be easily seen the next morning. The male flowers of the diploid male parent are collected in the morning before they are open and visited by pollinating insects. The covered female flowers of the tetraploid female parent, which have opened, are uncovered and pollinated with the collected fresh male flowers of the diploid male parent, starting after the male flower sheds pollen. The pollinated female flowers are again covered after pollination to prevent bees and any other insect visits. The pollinated female flowers are also marked. Generally, only the marked fruits are harvested for extracting triploid hybrid seed.

Bee-Pollination Method

Bee pollination can also be used in triploid watermelon production. In an exemplary bee-pollination method, the tetraploid female parent 51WA009 and the diploid male parent are typically planted in a ratio of 2 rows tetraploid parent to 1 row male parent. The female tetraploid plants are pruned to 2-3 branches. All of the male flower buds on the female tetraploid parent plants are removed manually (the de-budding process) during the pollination season, typically on a daily basis. Beehives are placed in the field for transfer of pollen by bees from the male parent to the female flowers of the female parent. Fruits set during this de-budding time are marked. Generally, only the marked fruits are harvested for extracting hybrid triploid seed.

Additional Breeding Methods.

This invention is also directed to methods for producing a watermelon plant by crossing a first parent watermelon plant with a second parent watermelon plant wherein the first or second parent watermelon plant is a plant of watermelon line 51WA009. Further, both first and second parent watermelon can come from watermelon line 51WA009. Thus, any of the following exemplary methods using watermelon line 51WA009 are part of this invention: selfing, backcrosses, hybrid production, crosses to populations, double haploid production, and the like. All plants produced using watermelon line 51WA009 as at least one parent are within the scope of this invention, including those developed from watermelon plants derived from watermelon line 51WA009. Advantageously, watermelon line 51WA009 can be used in crosses with other, different, watermelon plants to produce first generation ($F_1$) watermelon hybrid seeds and plants with desirable characteristics. The watermelon plants of the invention can also be used for transformation where exogenous transgenes are introduced and expressed by the plants of the invention. Genetic variants created either through traditional breeding methods or through transformation of the cultivars of the invention by any of a number of protocols known to those of skill in the art are intended to be within the scope of this invention.

The following describes exemplary breeding methods that may be used with watermelon line 51WA009 in the development of further watermelon plants. One such embodiment is a method for developing watermelon line 51WA009 progeny watermelon plants in a watermelon plant breeding program comprising: obtaining a plant, or a part thereof, of watermelon line 51WA009, utilizing said plant or plant part as a source of breeding material, and selecting a watermelon line 51WA009 progeny plant with molecular markers in common with watermelon line 51WA009 and/or with some, all or essentially all morphological and/or physiological characteristics of watermelon line 51WA009 (see, e.g., Tables 1 to 3). In representative embodiments, the progeny plant has at least 1, 2, 3, 4, 5, 6, 7, 8, 9, 10 or more of the morphological and physiological characteristics of watermelon line 51WA009 (for example, one or more of one or more of tetraploidy, round fruits, mature fruits having a solid light grey (e.g., Charleston grey) skin color, mature fruits having an intermediate rind thickness, mature fruits having dark red flesh (e.g., darker red as compared with line 4XHDML6), mature fruits with a lower weight than the mature fruits of line 4XHDML6, mature fruits that are more uniform in weight and/or shape than the mature fruits of line 4XHDML6, and/or resistance to Fusarium wilt race 1, e.g., as described in Tables 1 to 3), or even all of the morphological and physiological characteristics of watermelon line 51WA009 so that said progeny watermelon plant is not significantly different for said traits than watermelon line 51WA009, as determined at the 5% significance level when grown in the same environmental conditions; optionally, with the presence of one or more desired additional traits (e.g., male sterility, disease resistance, pest or insect resistance, herbicide resistance, and the like). Breeding steps that may be used in the breeding program include pedigree breeding, backcrossing, mutation breeding and/or recurrent selection. In conjunction with these steps, techniques such as RFLP-enhanced selection, genetic marker enhanced selection (for example, SSR markers) and/or and the making of double haploids may be utilized.

Another representative method involves producing a population of watermelon line 51WA009 progeny plants, comprising crossing watermelon line 51WA009 with another watermelon plant, thereby producing a population of watermelon plants that, on average, derives at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from watermelon line 51WA009, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of watermelon line 51WA009. One embodiment of this invention is the watermelon plant produced by this method and that has obtained at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from watermelon line 51WA009, and optionally may be the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and or double haploid technology.

One of ordinary skill in the art of plant breeding would know how to evaluate the traits of two plant varieties to determine if there is or is not significant difference between the two traits expressed by those varieties. For example, see Fehr and Walt, Principles of Cultivar Development, pp. 261-286 (1987). Thus, the invention includes watermelon line 51WA009 progeny watermelon plants characterized by e.g., one or more of one or more of tetraploidy, round fruits, mature fruits having a solid light grey (e.g., Charleston grey) skin color, mature fruits having an intermediate rind thickness, mature fruits having dark red flesh (e.g., darker red as compared with line 4XHDML6), mature fruits with a lower weight than the mature fruits of line 4XHDML6, mature fruits that are more uniform in weight and/or shape than the mature fruits of line 4XHDML6, and/or resistance to Fusarium wilt race 1. In embodiments, the invention encompasses progeny plants having a combination of at least 2, 3, 4, 5, 6, 7, 8, 9, 10 or more of the characteristics as described herein for watermelon line 51WA009, so that said progeny watermelon plant is not significantly different for said traits than watermelon line 51WA009, as determined at the 5% significance level when grown in the same environmental conditions. Using techniques described herein and those known in the art, molecular markers may be used to identify said progeny plant as progeny of watermelon line 51WA009. Mean trait values may be used to determine whether trait differences are significant, and optionally the traits are measured on plants grown under the same environmental conditions.

Progeny of watermelon line 51WA009 may also be characterized through their filial relationship with watermelon line 51WA009, as for example, being within a certain number of breeding crosses of watermelon line 51WA009. A breeding cross is a cross made to introduce new genetics into the progeny, and is distinguished from a cross, such as a self or a sib cross or a backcross to 51WA009 as a recurrent parent, made to select among existing genetic alleles. The lower the number of breeding crosses in the pedigree, the closer the relationship between watermelon line 51WA009 and its progeny. For example, progeny produced by the methods described herein may be within 1, 2, 3, 4, 5 or more breeding crosses of watermelon line 51WA009.

In representative embodiments, a watermelon plant derived from watermelon line 51WA009 comprises cells comprising at least one set of chromosomes derived from watermelon line 51WA009. In embodiments, the watermelon plant or population of watermelon plants derived from watermelon line 51WA009 comprises, on average, at least 6.25%, 12.5%, 25%, 30%, 35%, 40%, 45%, 50%, 55%, 60%, 65%, 70%, 80%, 85%, 90%, 95%, 96%, 97%, 98%) or 99% of its alleles (i.e., TAC) from watermelon line 51WA009, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of watermelon line 51WA009, and optionally may be the result of one or more of selfing, sibbing, backcrossing and/or double haploid techniques in any combination. In embodiments, the watermelon plant derived from watermelon line 51WA009 is one, two, three, four, five or more breeding crosses removed from watermelon line 51WA009.

In representative embodiments, a plant derived from watermelon line 51WA009 is a double haploid plant, a hybrid plant, an inbred plant, a tetraploid plant, a triploid plant and/or a diploid plant.

In embodiments, a derived plant from watermelon line 51WA009 comprises a desired added trait. In representative embodiments, a watermelon plant derived from watermelon line 51WA009 comprises all of the morphological and physiological characteristics of watermelon line 51WA009 (e.g., as described in Tables 1 to 3). In embodiments, the watermelon plant derived from watermelon line 51WA009 comprises essentially all of the morphological and physiological characteristics of watermelon line 51WA009 (e.g., as described herein), with the addition of a desired added trait.

According to the invention, tetraploid inbreds can be used as parental lines to develop new tetraploid lines. The unique and desirable traits of 51WA009 make it useful as a parental line in the development of new tetraploid inbreds. 51WA009 can be used as either female or male parent to cross with another tetraploid watermelon (e.g., and inbred or hybrid tetraploid) to develop new tetraploid inbreds.

Those skilled in the art will appreciate that any of the traits described herein with respect to plant transformation methods can be introduced into a plant of the invention (e.g., watermelon line 51WA009 and hybrid watermelon plants and other watermelon plants derived therefrom) using breeding techniques.

Genetic Transformation.

With the advent of molecular biological techniques that have allowed the isolation and characterization of genes that encode specific protein products, scientists in the field of plant biology developed a strong interest in engineering the genome of plants to contain and express foreign nucleic acids including additional or modified versions of native (endogenous) nucleic acids (optionally driven by a non-native promoter) in order to alter the traits of a plant in a specific manner. Any nucleic acid sequences, whether from a different species, the same species or an artificial sequence, which are introduced into the genome using transformation or various breeding methods, are referred to herein collectively as "transgenes." Over the last fifteen to twenty years, several methods for producing transgenic plants have been developed, and in particular embodiments the present invention also relates to transformed versions of watermelon plants disclosed herein.

Genetic engineering techniques can be used (alone or in combination with breeding methods) to introduce one or more desired added traits into plant, for example, watermelon 51WA009 or progeny or watermelon plants derived thereof. Once a transgene has been introduction into a plant by genetic transformation, it can be transferred to other plants via conventional breeding.

Plant transformation generally involves the construction of an expression vector that will function in plant cells. Optionally, such a vector comprises one or more nucleic acids comprising a coding sequence for a polypeptide or an untranslated functional RNA under control of, or operatively linked to, a regulatory element (for example, a promoter). In representative embodiments, the vector(s) may be in the form of a plasmid, and can be used alone or in combination with other plasmids, to provide transformed watermelon plants using transformation methods as described herein to incorporate transgenes into the genetic material of the watermelon plant.

Additional methods include, but are not limited to, expression vectors introduced into plant tissues using a direct nucleic acid transfer method, such as microprojectile-mediated delivery (e.g., with a biolistic device), DNA injection, *Agrobacterium*-mediated transformation, electroporation, and the like. Transformed plants obtained from the plants (and parts and tissue culture thereof) of the invention are intended to be within the scope of this invention.

Expression Vectors for Plant Transformation—Selectable markers.

Expression vectors typically include at least one nucleic acid comprising or encoding a selectable marker, operably linked to a regulatory element (for example, a promoter) that allows transformed cells containing the marker to be either recovered by negative selection, e.g., inhibiting growth of cells that do not contain the selectable marker, or by positive selection, e.g., screening for the product encoded by the selectable marker. Many commonly used selectable markers for plant transformation are well known in the transformation art, and include, for example, nucleic acids that code for enzymes that metabolically detoxify a selective chemical agent which may be an antibiotic or an herbicide, or nucleic acids that encode an altered target which is insensitive to the inhibitor. Positive selection methods are also known in the art.

Commonly used selectable markers in plants include, but are not limited to: neomycin phosphotransferase II (nptII) conferring resistance to kanamycin, hygromycin phosphotransferase conferring resistance to the antibiotic hygromycin, bacterial selectable markers that confer resistance to antibiotics (e.g., gentamycin acetyl transferase, streptomycin phosphotransferase, and aminoglycoside-3'-adenyl transferase, selectable markers conferring resistance to herbicides (e.g., glyphosate, glufosinate, or bromoxynil). Selection of transformed plant cells can also be based on screening presumptively transformed plant cells rather than direct genetic selection of transformed cells for resistance to a toxic substance such as an antibiotic; such markers include without limitation alpha-glucuronidase (GUS), alpha-galactosidase, luciferase, and Green Fluorescent Protein (GFP) and mutant GFPs.

Expression Vectors for Plant Transformation—Promoters.

Transgenes included in expression vectors are generally driven by a nucleotide sequence comprising a regulatory element (for example, a promoter). Numerous types of promoters are well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells.

Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissue are referred to as "tissue-specific." A "cell type" specific promoter preferentially drives expression in certain cell types in one or more organs, for example, vascular cells in roots or leaves. An "inducible" promoter is a promoter that is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

Many suitable promoters are known in the art and can be selected and used to achieve the desired outcome.

Signal Sequences for Targeting Proteins to Subcellular Compartments.

Transport of polypeptides produced by transgenes to a subcellular compartment such as the chloroplast, vacuole, peroxisome, glyoxysome, cell wall, or mitochondrion, or for secretion into the apoplast, is generally accomplished by means of operably linking a nucleotide sequence encoding a signal sequence to the 5' and/or 3' region of a nucleic acid encoding the polypeptide of interest. Signal sequences at the 5' and/or 3' end of the coding sequence target the polypeptide to particular subcellular compartments.

The presence of a signal sequence can direct a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J, 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Foreign Polypeptide Transgenes and Agronomic Transgenes.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign polypeptide then can be extracted from a tissue of interest or from total biomass. Protein extraction from plant biomass can be accomplished by known methods which are discussed, for example, by Heney and Orr, Anal. Biochem., 114:92-6 (1981). According to a representative embodiment, the transgenic plant provided for commercial production of foreign protein is a watermelon plant of the invention. In another embodiment, the biomass of interest is seed and/or fruit.

Likewise, by means of the present invention, agronomic transgenes and other desired added traits can be expressed in transformed plants (and their progeny, e.g., produced by breeding methods). More particularly, plants can be genetically engineered to express various phenotypes of agronomic interest or other desired added traits. Exemplary nucleic acids of interest in this regard conferring a desired added trait(s) include, but are not limited to, those transgenes that confer resistance to confer resistance to plant pests (e.g., nematode or insect) or disease (e.g., fungal, bacterial or viral), transgenes that confer herbicide tolerance, transgenes that confer male sterility, and transgenes that confer or contribute to a value-added trait such as increased nutrient content (e.g., iron, nitrate), increased sweetness (e.g., by introducing a transgene coding for monellin), modified fatty acid metabolism (for example, by introducing into a plant an antisense sequence directed against stearyl-ACP desaturase to increase stearic acid content of the plant), modified carbohydrate composition (e.g., by introducing into plants a transgene coding for an enzyme that alters the branching pattern of starch), modified fruit color (e.g., external fruit color and/or fruit flesh), or modified flavor profile of the fruit.

In embodiments, the transgene encodes a non-translated RNA (e.g., RNAi) that is expressed to produce targeted inhibition of gene expression, thereby conferring the desired trait on the plant.

In embodiments, the transgene encodes the machinery used for gene editing techniques.

Any transgene, including those exemplified above, can be introduced into the watermelon plants of the invention through a variety of means including, but not limited to, transformation (e.g., genetic engineering techniques), conventional breeding, and introgression methods to introduce the transgene into other genetic backgrounds.

Methods for Plant Transformation.

Numerous methods for plant transformation have been developed, including biological and physical plant transformation protocols. See, for example, Miki, et al., "Procedures for Introducing Foreign DNA into Plants" in Methods in Plant Molecular Biology and Biotechnology, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson Eds., CRC Press, Inc., Boca Raton, pp. 89-119 (1993). Commonly used plant transformation methods include *agrobacterium*-mediated transformation and direct transgene transfer methods (e.g., microprojectile-mediated transformation, sonication, liposome or spheroplast fusion, and electroporation of protoplasts or whole cells).

Following transformation of plant target tissues, expression of selectable marker transgenes (e.g., as described above) allows for preferential selection of transformed cells, tissues and/or plants, using regeneration and selection methods now well known in the art.

The foregoing methods for transformation are typically used to produce a transgenic watermelon line. The transgenic watermelon line can then be crossed with another (non-transgenic or transgenic) line in order to produce a new transgenic watermelon line. Alternatively, a transgene that has been engineered into a particular plant using transformation techniques can be introduced into another plant or line using traditional breeding (e.g., backcrossing) techniques that are well known in the plant breeding arts. For example, a backcrossing approach can be used to move an engineered transgene from a public, non-elite inbred line into an elite inbred line, or from an inbred line containing a foreign transgene in its genome into an inbred line or lines which do not contain that transgene. As used herein, "crossing" can refer to a simple X by Y cross, or the process of backcrossing, depending on the context.

Locus Conversion.

When the term "plant" is used in the context of the present invention, this term also includes any locus conversions of that plant or variety. The term "locus converted plant" as used herein refers to those plants that are developed, for example, by backcrossing, genome editing, genetic transformation and/or mutation, wherein essentially all of the desired morphological and physiological characteristics of a variety (e.g., one or more of tetraploidy, round fruits, mature fruits having a solid light grey [e.g., Charleston grey] skin color, mature fruits having an intermediate rind thickness, mature fruits having dark red flesh (e.g., darker red as compared with line 4XHDML6), mature fruits with a lower weight than the mature fruits of line 4XHDML6, mature fruits that are more uniform in weight and/or shape than the mature fruits of line 4XHDML6, and/or resistance to *Fusarium* wilt race 1) are recovered in addition to the one or more genes introduced into the variety. To illustrate, backcrossing methods can be used with the present invention to improve or introduce a characteristic into the variety. The term "backcrossing" as used herein refers to the repeated crossing of a hybrid progeny back to the recurrent parent, e.g., backcrossing 1, 2, 3, 4, 5, 6, 7, 8, 9, or more times to the recurrent parent. The parental plant that contributes the gene for the desired characteristic is termed the "nonrecurrent" or "donor parent." This terminology refers to the fact that the nonrecurrent parent is generally used one time in the breeding e.g., backcross) protocol and therefore does not recur. The gene that is transferred can be a native gene, a mutated native gene or a transgene introduced by genetic engineering techniques into the plant (or ancestor thereof). The parental plant into which the gene(s) from the nonrecurrent parent are transferred is known as the "recurrent" parent as it is used for multiple rounds in the backcrossing protocol. Poehlman & Sleper (1994) and Fehr (1993). In a typical backcross protocol, the original variety of interest (recurrent parent) is crossed to a second variety (nonrecurrent parent) that carries the gene(s) of interest to be transferred. The resulting progeny from this cross are then crossed again to the recurrent parent and the process is repeated until a plant is obtained wherein essentially all of the desired morphological and physiological characteristics of the recurrent parent are recovered in the converted plant in addition to the transferred gene(s) and associated trait(s) from the nonrecurrent parent.

Genetic Analysis of Watermelon Line 51WA009.

The invention further provides a method of determining a genetic characteristic of watermelon line 51WA009 or a progeny thereof, e.g., a method of determining a genotype of watermelon line 51WA009 or a progeny thereof. In embodiments, the method comprises detecting in the genome of a 51WA009 plant, or a progeny plant thereof, at least a first polymorphism (e.g., by detecting a nucleic acid marker by a method comprising nucleic acid amplification and/or nucleic acid sequencing). To illustrate, in embodiments, the method comprises obtaining a sample of nucleic acids from the plant and detecting at least a first polymorphism in the nucleic acid sample. Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

DEPOSIT INFORMATION

Applicants have made a deposit of at least 2500 seeds of watermelon line 51WA009 with the American Type Culture Collection (ATCC), 10801 University Boulevard, Manassas, Va., 20110-2209 U.S.A. under ATCC Deposit No PTA-126082 on Oct. 1, 2019. This deposit of watermelon variety 51WA009 will be maintained in the ATCC depository, which is a public depository, for a period of 30 years, or 5 years after the most recent request, or for the effective life of the patent, whichever is longer, and will be replaced if any of the deposited seed becomes nonviable during that period. Additionally, Applicants have satisfied all the requirements of 37 C.F.R. §§ 1.801-1.809, including providing an indication of the viability of the samples. Access to this deposit will be made available during the pendency of this application to the Commissioner upon request. Upon the issuance of a patent on the variety, the variety will be irrevocably and without restriction released to the public by providing access to the deposit of at least 2500 seeds of the variety with the ATCC. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC § 2321 et seq.).

The foregoing invention has been described in detail by way of illustration and example for purposes of clarity and understanding. However, it will be apparent that certain changes and modifications such as single locus modifications and mutations, somaclonal variants, variant individuals selected from large populations of the plants of the instant inbred and the like may be practiced within the scope of the invention.

What is claimed is:

1. A seed of tetraploid watermelon line 51WA009, a representative sample of seed having been deposited under ATCC Accession No. PTA-126082.

2. A plant of tetraploid watermelon line 51WA009, a representative sample of seed having been deposited under ATCC Accession No. PTA-126082.

3. A watermelon plant, or a part thereof, having all the physiological and morphological characteristics of the watermelon plant of claim 2.

4. A seed that produces the plant of claim 3.

5. A plant part of the plant of claim 2, wherein the plant part is a fruit, an F1 seed, a scion, a rootstock, a shoot, pollen, an ovule, an anther, a root, or a cell.

6. A tissue culture of regenerable cells of the watermelon plant of claim 2.

7. A converted watermelon plant produced by introducing a single locus conversion into the plant of claim 2, wherein said converted watermelon plant comprises said single locus conversion and otherwise comprises all of the physiological and morphological characteristics of watermelon line 51WA009.

8. A seed that produces the plant of claim 7.

9. A method of producing watermelon seed, the method comprising crossing the plant of claim 2 with itself or a second watermelon plant and harvesting the resulting seed.

10. An F1 seed produced by the method of claim 9.

11. A watermelon plant, or a fruit thereof, produced by growing the seed of claim 10.

12. A method of producing a watermelon plant, the method comprising growing a diploid reversion of a watermelon plant produced by growing the watermelon seed of claim 9.

13. The method according to claim 12, further comprising the step of doubling the chromosome number of said diploid reversion to produce a tetraploid watermelon plant.

14. A method of developing a watermelon line in a watermelon plant breeding program using plant breeding techniques, which include employing a watermelon plant, or its parts, as a source of plant breeding material, comprising:
  (a) obtaining the watermelon plant, or its parts, of claim 2 as a source of breeding material; and
  (b) applying plant breeding techniques.

15. A method for producing a seed of a watermelon plant derived from the plant of claim 2, the method comprising:
  (a) crossing a plant of watermelon line 51WA009 with a second watermelon plant; and
  (b) allowing seed to form;
  (c) growing a plant from the seed of step (b) to produce a plant derived from watermelon line 51WA009;
  (d) selfing the plant of step (c) or crossing it to a second watermelon plant to form additional watermelon seed derived from watermelon line 51WA009; and
  (e) optionally repeating steps (c) and (d) one or more times to generate further derived watermelon seed from watermelon line 51WA009, wherein in step (c) a plant is grown from the additional watermelon seed of step (d) in place of growing a plant from the seed of step (b).

16. A method of vegetatively propagating the plant of claim 2, the method comprising:
  (a) collecting tissue capable of being propagated from a plant of watermelon line 51WA009;
  (b) cultivating the tissue to obtain proliferated shoots; and
  (c) rooting the proliferated shoots to obtain rooted plantlets.

17. The method of claim 16, wherein the method further comprises growing plants from the rooted plantlets.

18. A method of introducing a desired added trait into watermelon line 51WA009, the method comprising:
  (a) crossing the plant of claim 2 with a watermelon plant that comprises a desired added trait to produce F1 progeny;
  (b) selecting an F1 progeny that comprises the desired added trait;
  (c) crossing the selected F1 progeny with watermelon line 51WA009 to produce backcross progeny;
  (d) selecting a backcross progeny comprising the desired added trait and otherwise all of the physiological and morphological characteristics of the watermelon line 51WA009; and
  (e) optionally repeating steps (c) and (d) one or more times to produce a plant derived from watermelon line 51WA009 comprising a desired added trait and otherwise all of the physiological and morphological characteristics of watermelon line 51WA009, wherein in step (c) the selected backcross progeny produced in step (d) is used in place of the selected F1 progeny of step (b).

19. A watermelon plant produced by the method of claim 18 or a selfed progeny thereof, wherein said watermelon plant or selfed progeny thereof has the desired added trait and otherwise has all of the physiological and morphological characteristics of watermelon line 51WA009.

20. A seed that produces the plant of claim 19.

21. A method of producing a plant of watermelon line 51WA009 comprising a desired added trait, the method comprising introducing a transgene conferring the desired trait into the plant of claim 2.

22. A watermelon plant produced by the method of claim 21 or a selfed progeny thereof, wherein said watermelon plant or selfed progeny thereof comprises the transgene and has the desired added trait and otherwise has all of the physiological and morphological characteristics of watermelon line 51WA009.

23. A seed that produces the plant of claim 22.

24. A method of producing triploid watermelon seed, the method comprising:
(a) crossing the watermelon plant of claim 2 with a diploid watermelon plant; and
(b) harvesting the resultant triploid watermelon seed.

25. An F1 triploid watermelon seed produced by the method of claim 24.

26. An F1 triploid watermelon plant, or fruit thereof, produced from the seed of claim 25.

27. A method of producing seedless watermelon fruit, the method comprising:
(a) crossing the triploid plant of claim 26 and a diploid watermelon plant;
(b) allowing seedless fruit to form; and
(c) harvesting the seedless fruit.

28. A method of producing a tetraploid watermelon plant, the method comprising crossing the plant of claim 2 with a different tetraploid watermelon plant.

29. An F1 tetraploid watermelon plant, or a fruit thereof, produced by the method of claim 28.

30. A method of determining a genotype of watermelon line 51WA009, the method comprising:
(a) obtaining a sample of nucleic acids from the plant of claim 2; and
(b) detecting a polymorphism in the nucleic acid sample.

* * * * *